(12) United States Patent
Peintner et al.

(10) Patent No.: US 12,714,089 B1
(45) Date of Patent: Aug. 25, 2026

(54) AUTONOMOUS SOIL SAMPLING AND HERBICIDE APPLICATION

(71) Applicant: Elemental Agronomy, Denver, CO (US)

(72) Inventors: Bart Michael Peintner, Denver, CO (US); Adam Schroeder, Monclova, OH (US); Blaine Joersz, Denver, CO (US)

(73) Assignee: ELEMENTAL AGRONOMY, Denver, CO (US)

( * ) Notice: Subject to any disclaimer, the term of this patent is extended or adjusted under 35 U.S.C. 154(b) by 0 days.

(21) Appl. No.: 19/331,725

(22) Filed: Sep. 17, 2025

(51) Int. Cl.
*A01M 21/04* (2006.01)
*B05B 12/12* (2006.01)
*B05B 13/00* (2006.01)
*G01N 33/00* (2006.01)
*G05D 1/667* (2024.01)
*G05D 107/20* (2024.01)

(52) U.S. Cl.
CPC .......... *A01M 21/043* (2013.01); *B05B 12/12* (2013.01); *B05B 13/005* (2013.01); *G01N 33/0098* (2013.01); *G05D 1/667* (2024.01); *G05D 2107/20* (2024.01)

(58) Field of Classification Search
CPC . A01M 21/043; G05D 1/667; G05D 2107/20; G01N 33/0098; B05B 12/12; B05B 13/005
See application file for complete search history.

(56) References Cited

U.S. PATENT DOCUMENTS

| | | | | |
|---|---|---|---|---|
| 9,655,356 B1 * | 5/2017 | Lytle, Jr. | ............... | A01M 17/00 |
| 2023/0148585 A1 * | 5/2023 | Singleton | ............... | A01G 25/16 47/1.7 |
| 2023/0206627 A1 * | 6/2023 | Germain | ............... | G06V 10/82 47/1.7 |
| 2023/0276782 A1 * | 9/2023 | Schuh | ............... | A01M 7/0089 47/1.7 |
| 2023/0292737 A1 * | 9/2023 | Thompson | .......... | A01M 7/0089 47/1.7 |
| 2024/0032525 A1 * | 2/2024 | Petro | ............... | G06T 7/0012 |

FOREIGN PATENT DOCUMENTS

| | | | |
|---|---|---|---|
| CN | 101707992 A * | 5/2010 | |
| WO | WO-02088679 A1 * | 11/2002 | .......... A01M 7/0089 |

* cited by examiner

*Primary Examiner* — Monica L Perry
*Assistant Examiner* — Aaron M Rodziwicz
(74) *Attorney, Agent, or Firm* — NICHOLSON DE VOS WEBSTER & ELLIOTT LLP

(57) ABSTRACT

An autonomous herbicide applicator system includes detecting, at a first time, a weed at a first location within a field. The system identifies one or more characteristics of the weed and/or environment and determines an herbicide application strategy for the weed based on the one or more characteristics. The system activates a solenoid to enable a flow of herbicide via an applicator nozzle to treat the weed in accordance with the herbicide application strategy. The system navigates back to the first location from another location at a second time and detects a condition of the weed. The system updates the herbicide application strategy for the one or more characteristics in response to the condition of the weed at the second time. The updating causes the system to change how herbicide is subsequently applied to weeds having the one or more characteristics.

20 Claims, 8 Drawing Sheets

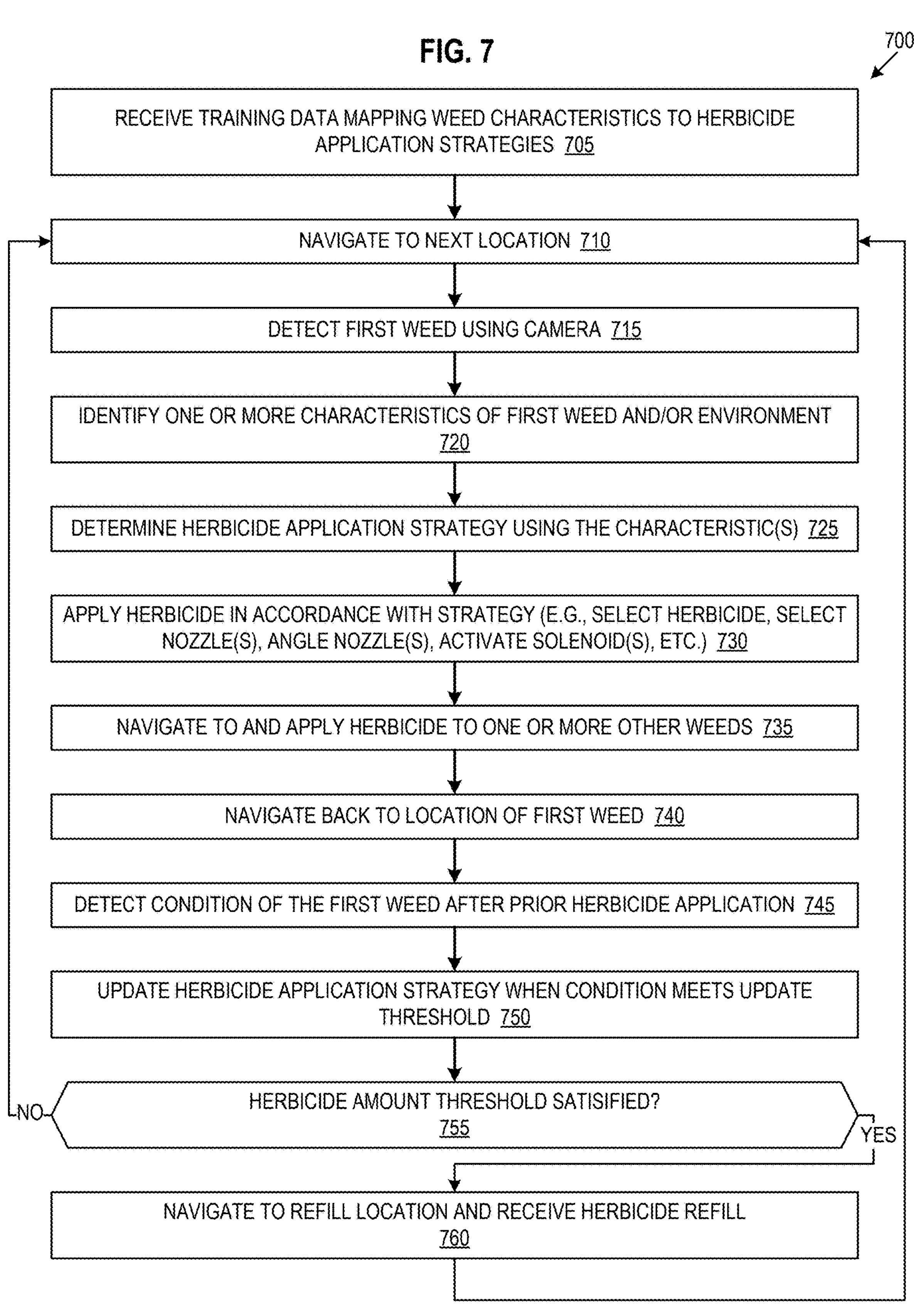
FIG. 7
700
RECEIVE TRAINING DATA MAPPING WEED CHARACTERISTICS TO HERBICIDE APPLICATION STRATEGIES 705
NAVIGATE TO NEXT LOCATION 710
DETECT FIRST WEED USING CAMERA 715
IDENTIFY ONE OR MORE CHARACTERISTICS OF FIRST WEED AND/OR ENVIRONMENT 720
DETERMINE HERBICIDE APPLICATION STRATEGY USING THE CHARACTERISTIC(S) 725
APPLY HERBICIDE IN ACCORDANCE WITH STRATEGY (E.G., SELECT HERBICIDE, SELECT NOZZLE(S), ANGLE NOZZLE(S), ACTIVATE SOLENOID(S), ETC.) 730
NAVIGATE TO AND APPLY HERBICIDE TO ONE OR MORE OTHER WEEDS 735
NAVIGATE BACK TO LOCATION OF FIRST WEED 740
DETECT CONDITION OF THE FIRST WEED AFTER PRIOR HERBICIDE APPLICATION 745
UPDATE HERBICIDE APPLICATION STRATEGY WHEN CONDITION MEETS UPDATE THRESHOLD 750
HERBICIDE AMOUNT THRESHOLD SATISIFIED? 755
NO
YES
NAVIGATE TO REFILL LOCATION AND RECEIVE HERBICIDE REFILL 760

800
PROCESSING DEVICE
802
INSTRUCTIONS
826
CONTROL SYSTEM
835
STATIC MEMORY
806
BUS 830
MAIN MEMORY
804
INSTRUCTIONS
826
CONTROL SYSTEM
835
DATA STORAGE SYSTEM
818
MACHINE-READABLE MEDIUM
824
INSTRUCTIONS
826
CONTROL SYSTEM
835
NETWORK
INTERFACE DEVICE
808
NETWORK
820

AUTONOMOUS SOIL SAMPLING AND HERBICIDE APPLICATION

TECHNICAL FIELD

The present disclosure generally relates to autonomous farming operations, and more specifically, relates to a robotic platform to autonomously sample soil fertility and/or implement precise herbicide/fertilization application.

BACKGROUND

Soil fertility and weed control are vital to agricultural yields. Soil fertility refers to the ability of soil to sustain agricultural plant growth. Soil fertilization is the process of supplementing the existing soil with additional nutrients. Appropriate nutrient management is crucial to agronomic systems. For example, soil fertilization may seek to achieve a balance of nitrogen, phosphorus, potassium, magnesium, and/or calcium in the soil for crop production. Undesirable plants (i.e., weeds) compete with crop plants, impede water flow, increase the risk of disease, interfere with harvesting, and otherwise complicate the growing of crop plants. Weed control typically includes the application of herbicide chemicals. The disclosure will be understood more fully from the detailed description given below and from the accompanying drawings of various embodiments of the disclosure. The drawings, however, should not be taken to limit the disclosure to the specific embodiments, but are for explanation and understanding only.

BRIEF DESCRIPTION OF THE DRAWINGS

FIG. 7 is a flow diagram of an example method of herbicide application in accordance with some embodiments of the present disclosure.

DETAILED DESCRIPTION

Figure 1:
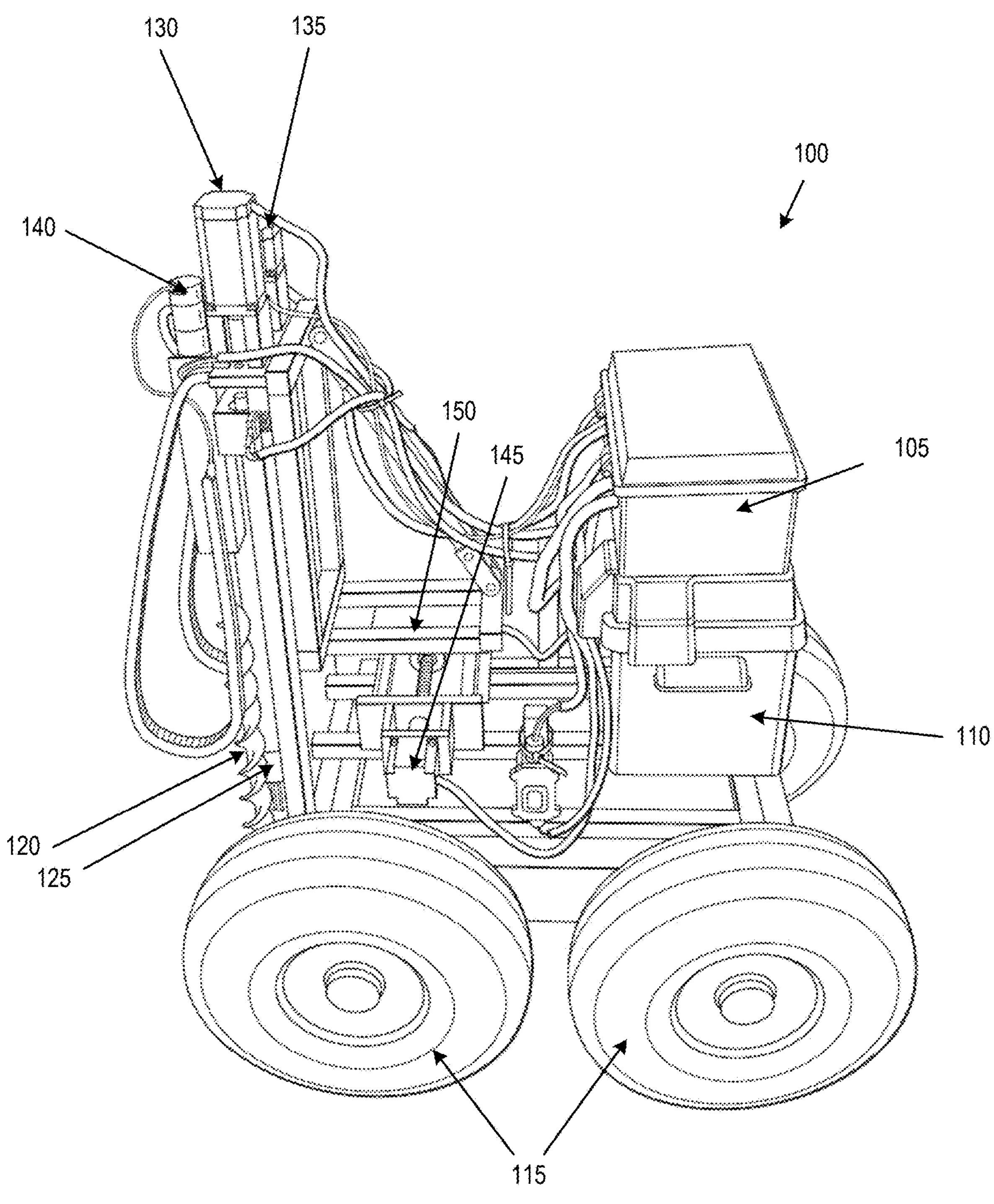
FIG. 1 illustrates an autonomous soil sampling system in accordance with some embodiments of the present disclosure.

Aspects of the present disclosure are directed to autonomous farming operations. These systems can address soil fertility as well as weed control. Laboratory-based (lab-based) soil testing provides clarity on soil fertility. This testing, however, is slow and expensive. This expense grows as the granularity of testing different portions of land and/or soil depths increases. Working without this clarity, on the other hand, typically leads to adding excess supplements. Excess fertilization is wasteful/costly, negatively impacts the soil, and has undesirable environmental impacts. For example, an excess of nitrogen inhibits microbes and fungus and generally leads to long-term degradation of the soil.

Soil electrical conductivity (EC) testing is a less expensive alternative to lab-based soil testing. EC measures how well soil can conduct an electrical current, which serves as an indication of the availability of nutrients in the soil. Soil texture, organic matter content, salinity, clay content, moisture content, temperature, soil acidity or basicity (potential of hydrogen or pH), etc., however, can also impact soil EC measurements and nutrient availability. As a result, EC is a relative measurement of soil fertility and has limited value in conventional use.

Aspects of the present disclosure address the above and other deficiencies via a mobile, automated fertilization system sampling the soil, using known fertilization and/or water deposit amounts to convert raw EC measurements into consistent, absolute values, and generating precise fertilization mappings. For example, a limited number of laboratory-based samples can provide an initial calibration of corresponding EC measurements for the system. The system uses a known amount of water (e.g., manually deposited and/or due to rainfall) and uses known water content curves to further refine this calibration. Additionally, the system can employ a machine learning algorithm and the refined calibration data as training data to correlate subsequent raw measurements (e.g., EC, temperature, etc.) and known added nutrient and/or water amounts to determine absolute nutrient values. The system can further use imaging data, pH sampling, sample depth, nutrient application depth, nutrient application methods, etc. to refine the soil model(s). As a result, the system can provide precise fertilization guidance to a user, send fertilization instructions to external mechanical nutrient applicators, initiate onboard mechanical nutrient applicators, and/or generate an order for fertilization supplies.

Similar to fertilization, agronomic systems include the application of herbicides to inhibit the growth of weeds that can impact yields. Historically, herbicides would be applied to entire fields. This was often based on a single rate of application and a single mix of herbicides (e.g., per field). To lower costs and minimize negative effects of herbicide applications, such as potential harm to the desired crops, chemical run-off, etc., systems have developed to refine the process via variable rates of application per field and by targeting the weeds rather than spraying the entire field. Conventional approaches, however, maintain the large form factors that were developed to minimize human labor. For example, a conventional applicator system for weed control can commonly be between twenty and forty meters in width. Accordingly, conventional systems are limited to traveling over crops as they are too wide to navigate between rows and/or individual plants. Additionally, these large-scale systems can lack precision to address individual weeds/groups of weeds within the same area but that grow at different rates/times, have varied proximity to the crop/desirable plant, etc.

Aspects of the present disclosure address the above and other deficiencies via a mobile, automated weed control system sized to freely navigate crop rows and equipped to identify weeds, differentiate weeds based on type, size/maturity, stem location, proximity to crop plants, etc. The system uses a continuously variable applicator to dispense herbicides at rates based on these observed factors. Additionally, the system can automate experimentation of application of herbicides (e.g., flow rate, herbicide type, spray angle, system movement speed, temperature, etc.) and determine optimal treatment strategies for different combinations of the observed factors after application. Slow system speed (in terms of navigating crops/fields) enables the use of a low/variable flow rate in spraying herbicides, saving energy for the mobile platform. A system with small nozzles and a slow flow rate, however, can increase the likelihood of clogging. The system addresses this challenge by using machine learning to detect clogged applicator nozzles and/or pump failures, saving the cost and complexity of adding mechanical flow detectors. Using the observed factors and automated experimentation, the system can generate recommendations on a schedule of future applications, recommendations on herbicides (type and/or quantity) to use, summaries of weed densities, types, and distributions, schedule time and/or locations for herbicide refills, maintenance, and/or platform charging, support muti-field/user planning, and work within target goals of herbicide application limits, costs, etc.

Additional details and benefits of embodiments of these autonomous agronomic systems are set forth below with reference to the drawings.

FIG. 1 illustrates autonomous soil sampling system 100 in accordance with some embodiments of the present disclosure. Autonomous soil sampling system 100 is a mobile platform including a control system 105, power supply/battery 110, and wheels 115. Control system 105 processes inputs via sensors (navigation, positioning, etc.), wireless communication receiver(s), on-board buttons/switches, etc. For example, autonomous soil sampling system 100 includes navigation sensors (not illustrated). Navigation sensors can include one or more of cameras, infrared sensors, radar, light detection and ranging (LIDAR), etc. to enable control system 105 to detect obstacles and autonomously navigate a field via control of wheels 115, positioning data, mapping data, etc. Control system 105 generates outputs to, e.g., control one or more motors attached to wheels 115 and/or other onboard equipment (described below) to sample soil at various locations, transmit wireless communications, generate on-board displays, etc.

Autonomous soil sampling system 100 further includes a digging implement 120. For example, digging implement 120 can include one or more attached augers, spinning disks, chainsaw trenchers, drills, or other implements to displace soil. In contrast to a probe that requires significant force to reach relevant depths, digging implement 120 provides autonomous soil sampling system 100 with a low power attachment to sample soil at one or more depths below the ground surface. For example, autonomous soil sampling system 100 can adapt to different conditions and goals to measure at various depths for no-till cropping, conventional tillage, an expected depth of where organic matter and nutrient cycling occur, etc.

Autonomous soil sampling system 100 also includes electrometric sensor 125 or a similar sensor to measure electrical resistance and/or capacitance at the soil sample location. While electrometric sensor 125 is illustrated as a separate attachment from digging implement 120, some embodiments integrate electrometric sensor 125 as a component of/within digging implement 120. Electrometric sensor 125 can include one or more probes inserted into the soil at a depth within a hole created by digging implement 120. As one example, electrometric sensor 125 measures the ability of the soil to conduct an electrical current, which corresponds to the concentration of dissolved ions within the soil. Typically, the greater the amount of dissolved inorganic and organic substances present, the higher the electrometric value. In one embodiment, the electrometric sensor 125 generates readings in deciSiemens per meter (dS/m). Control system 105 uses the electrometric sensor 125 to map raw electrometric measurements into consistent, absolute values, as described in greater detail below.

Digging implement positioning motor 130 controls the vertical positioning of digging implement 120. For example, as digging implement 120 displaces soil, digging implement positioning motor 130 lowers digging implement 120 into the hole created by soil displacement. Similarly, electrometric sensor positioning motor 135 controls the vertical positioning of electrometric sensor 125. Electrometric sensor positioning motor 135 enables autonomous soil sampling system 100 to take soil sample readings at one or more depths within the hole created by digging implement 120. As described above, electrometric sensor 125 can be integrated with digging implement 120. In such an embodiment, digging implement positioning motor 130 serves to control the vertical position of both digging implement 120 and electrometric sensor 125.

Digging implement driving motor 140 activates digging implement 120. For example, when digging implement 120 includes one or more augers, driving motor 140 rotates the auger blade(s) to displace soil. Similarly, driving motor 140 can activate spinning disks, chainsaw trenching blades, or another embodiment of digging implement 120.

In some embodiments, autonomous soil sampling system 100 further includes horizontal positioning motor 145. For example, control system 105 can use digging implement positioning motor 130 to retract digging implement 120 from a hole, activate horizontal positioning motor 145 to drive support structure 150 to move electrometric sensor 125 over the newly created hole. As a result, autonomous soil sampling system 100 does not need to reposition the entire autonomous platform to lower electrometric sensor 125 to the desired sample depth.

Figure 2:
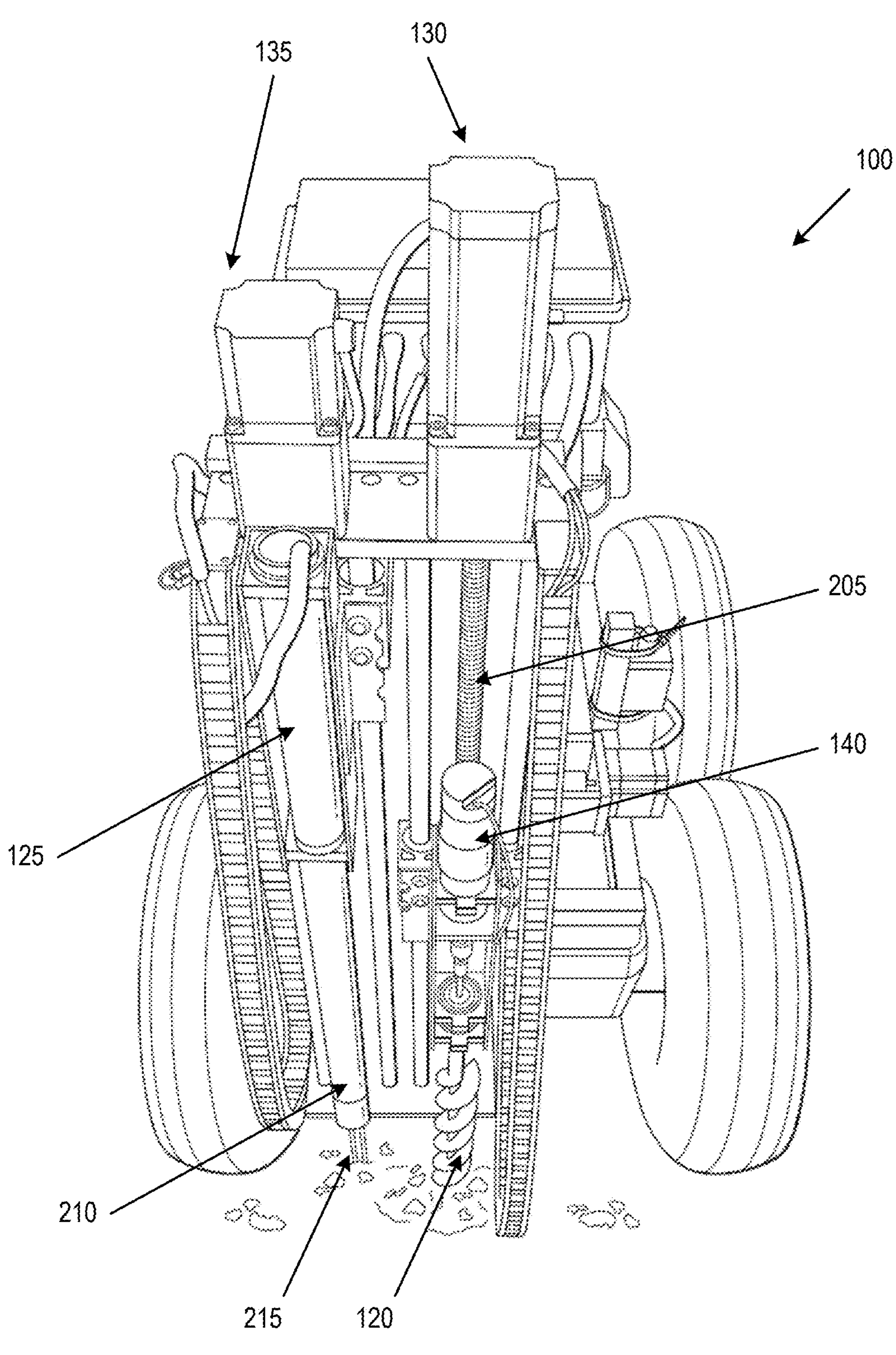
FIG. 2 illustrates another view of the autonomous soil sampling system in accordance with some embodiments of the present disclosure.

FIG. 2 illustrates another view of the autonomous soil sampling system 100 in accordance with some embodiments of the present disclosure. In this view, autonomous soil sampling system 100 has driven digging implement 120 into the soil by way of control system 105 controlling digging implement positioning motor 130, moving digging implement 120 vertically by rotating threaded column 205, and driving digging implement driving motor 140 to displace soil.

In the illustrated embodiment, electrometric sensor 125 is positioned above ground but extended for sake of explanation. In some embodiments, electrometric sensor 125 is retracted within protective housing 210 when not in use. As described above, electrometric sensor 125 includes one or more sensor probes 215. Sensor probes 215 are inserted into the soil at the desired depth by electrometric sensor positioning motor 135 to generate the raw soil conductivity reading.

Figure 3:
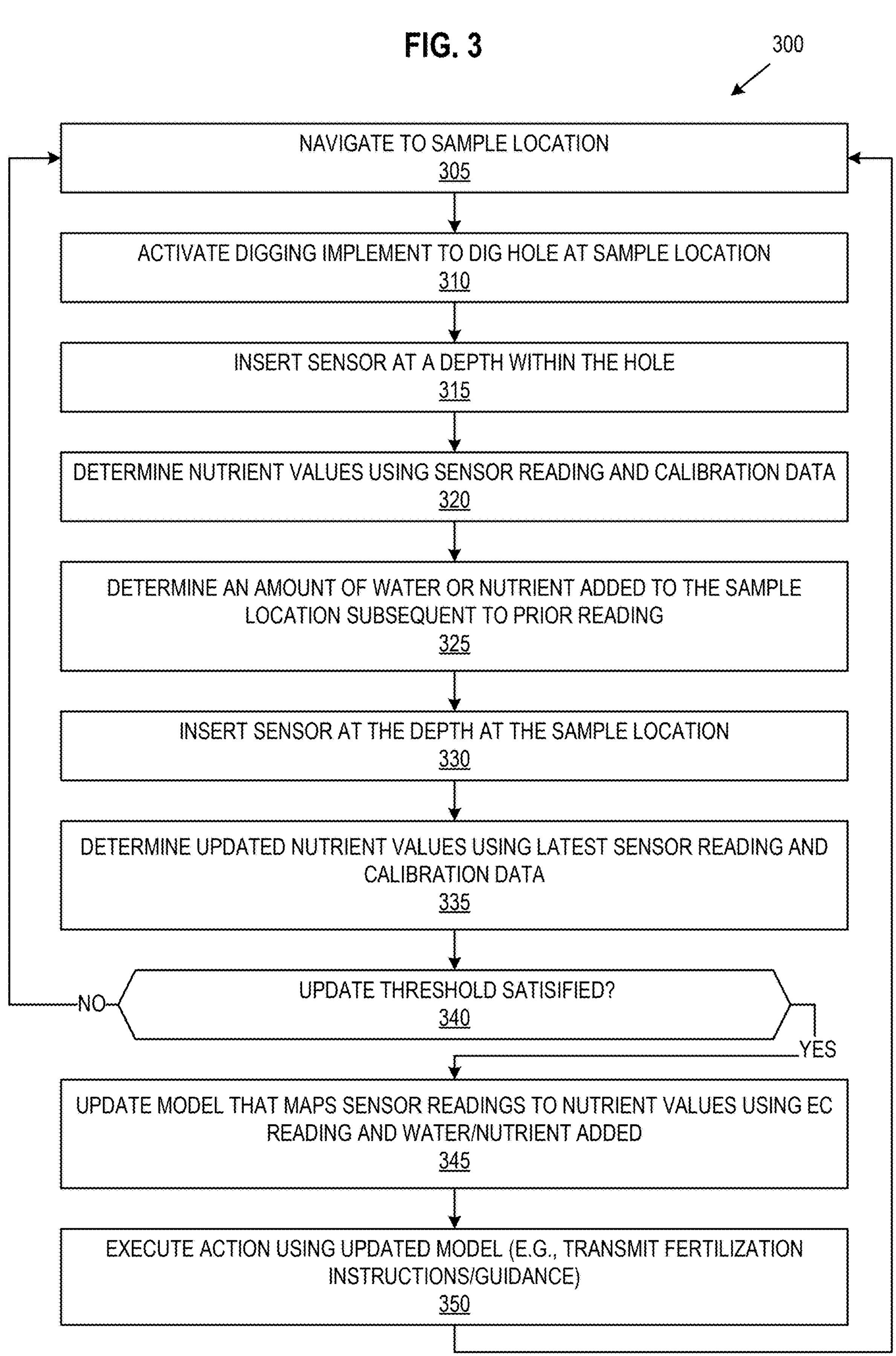
FIG. 3 is a flow diagram of an example method to sample soil fertility in accordance with some embodiments of the present disclosure.

FIG. 3 is a flow diagram of method 300 to sample soil fertility in accordance with some embodiments of the present disclosure. Method 300 can be performed by processing logic that can include hardware (e.g., processing device, circuitry, dedicated logic, programmable logic, microcode, hardware of a device, integrated circuit, etc.), software (e.g., instructions run or executed on a processing device), or a combination thereof. In some embodiments, method 300 is performed by control system 105. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At operation 305, control system 105 navigates autonomous soil sampling system 100 to a soil sample location. For example, control system 105 can use mapping data, its current location (e.g., determined via an onboard positional sensor), determine a path to a soil sample location, and generate motor outputs to control wheels 115 in conjunction with navigation sensors to drive autonomous soil sampling system 100 to the soil sample location. In some embodiments, soil sample locations are stored within a data structure by control system 105. For example, control system 105 can receive soil sample locations from a user and store the location data for use in navigation. In other embodiments, control system 105 determines soil sample locations based on stored parameters. For example, control system 105 can receive parameters from a user to sample a predetermined number of locations within a given field/boundary, sample locations at a predetermined spacing from one another, etc. and determine locations based on the received parameters. In one embodiment, control system 105 determines locations to obtain ten samples per acre, randomly or uniformly selecting locations within a given acre with the limitation of not harming existing crops, and at one or more depths.

At operation 310, control system 105 activates digging implement 120 to dig a hole at the soil sample location. For example, control system 105 uses a combination of digging implement positioning motor 130 and digging implement driving motor 140 to control digging implement 120 to displace soil to a sampling depth. In one embodiment digging implement 120 digs a hole to a depth of 6-18 inches.

In one embodiment, control system 105 stores one or more sampling depths per location (position, field, or bounded area such as an acre) for the location. In some embodiments, control system 105 receives a crop type for the location and looks up the one or more sampling depths in a stored data structure that maps crop types to one or more sampling depths. For example, control system 105 can target at least sampling at the root depth of a given crop type.

At operation 315, control system 105 inserts electrometric sensor 125 into soil within the hole. For example, in embodiments in which electrometric sensor 125 is separate from digging implement 120, control system 105 uses digging implement positioning motor 130 to retract digging implement 120 from the hole, horizontal positioning motor 145 to orient electrometric sensor 125 over the hole, and electrometric sensor positioning motor 135 to lower electrometric sensor 125 to the determined depth and insert sensor probes 215 into the soil at that depth.

At operation 320, control system 105 determines nutrient values at the soil sample location by taking an electrometric reading of the soil at the depth within the hole. For example, electrometric sensor 125 measures the ability of the soil to conduct an electrical current and generates a raw measurement reading (e.g., in dS/m). For example, most field crops and vegetables thrive in soil with a reading in the range of 0-4 dS/m. Readings below 0.2 dS/m may be indication of nutrient deficiency and readings above 4 dS/m may be indication of excess salinity.

In one embodiment, electrometric sensor 125 uses varying frequencies of electrical current to generate different measurement readings for different nutrients. For example, a spectrum of differing frequencies in the electrical current generated by electrometric sensor 125 and detected by sensor probes 215 can isolate different nutrients.

In one embodiment, control system 105 maps the raw measurement to one or more nutrient values using a model generated by a machine learning or similar algorithm. For example, a user can take soil samples from the location or surrounding area and send them out for lab testing. By using specialized conductivity meters in laboratory facilities, soil samples sent for lab-based assessment will yield very accurate results. These initial test results will serve as the initial calibration of the machine learning interpolation techniques to map raw measurement readings to nutrient values. Additionally, as described below, control system 105 can use the machine learning algorithm to update the mappings by using data indicating measured quantities of nutrients and/or water deposited in the soil and taking an updated electrometric reading.

In some embodiments, control system 105 uses additional data to map raw electrometric measurement data to nutrient values. For example, control system 105 can receive and use one or more of the following as additional inputs to the machine learning algorithm: weather conditions for the soil sample location, soil type and slope, image data of the soil sample location, historic crop yields at the soil sample location, soil reduction and oxidation (redox) potential at the soil sample location, varied depths of electrometric measurement values, and/or nutrient application depth.

At operation 325, control system 105 determines the amount of water and/or nutrient(s) added to the soil sample location at a subsequent time (i.e., subsequent to the first measurement taken in operation 320). In one embodiment, control system 105 deposits a measured quantity of water and/or nutrients. For example, autonomous soil sampling system 100 can further include a dispensing system similar to that described below with reference to FIGS. 4-6 and retrieve a saved value representing the deposited quantity of liquid. In other embodiments, control system 105 receives input including a measurement of water and/or nutrient(s) added to the soil sample location manually (e.g., via a user-controlled system, sprinklers, etc.), by another autonomous system (e.g., autonomous applicator system 400 described below), as the result of weather (e.g., a rain report).

In some embodiments, control system 105 performs at least a portion of soil sampling method 300 at one or more other locations before returning to retest a previously-sampled location. For example, control system 105 can execute operations 305-320 at multiple locations in sequence before returning to any of those locations and resuming method 300 at operation 325.

At operation 330, control system 105 inserts electrometric sensor 125 into soil within the hole at time after the deposit of nutrient(s)/water. For example, control system 105 can use an existing hole (e.g., created by operation 310) or create a new hole at the soil sample location (e.g., by repeating operation 310). Additionally, control system 105 inserts electrometric sensor 125 at the predetermined depth within the hole as described with reference to operation 315.

At operation 335, control system 105 determines updated nutrient values at the soil sample location by taking a second electrometric reading of the soil at the soil sample location. As described above, control system 105 maps the raw measurement to one or more nutrient values using the machine learning model described with reference to operation 320. For example, control system 105 determines an amount of nitrogen, phosphorus, potassium, magnesium, and/or calcium in the soil, pH of the soil, water content in the soil, etc.

At operation 340, control system 105 determines if the second electrometric reading satisfies an update threshold. For example, control system 105 can use a water content curve or other predetermined model to define an expected change or range of expected change in the one or more nutrient values due to the deposit of water and/or nutrient(s) determined at operation 325. Control system 105 determines the second electrometric reading satisfies the update threshold when, e.g., the nutrient value(s) determined as a result of the second electrometric reading vary from (exceed or fall below) the expected change/range of change by a threshold amount. If the second electrometric reading does not satisfy the update threshold, method 300 returns to operation 305 to navigate to another soil sample location. If the second electrometric reading satisfies the update threshold, method 300 proceeds to operation 345.

At operation 345, control system 105 updates the model that maps raw electrometric measurement value(s) to value(s) representing a quantity of one or more nutrients present in the soil. For example, control system 105 provides corrective input to the machine learning algorithm using the first electrometric reading, the amount of water/nutrient(s) added, and the second electrometric reading. Based on the water content curve or other predetermined model defining the expected change in nutrient value(s) in the second electrometric measurement value(s), the machine learning algorithm updates the model/mapping of raw electrometric measurement values to nutrient values. In one embodiment, control system 105 updates the model by using the machine learning algorithm to update one or more weight vectors using error-correction learning, gradient descent, back-propagation, or a similar learning algorithm. Control system 105 continues sampling soil with the updated model as method 300 returns to operation 305.

At operation 350, control system 105 executes an action using the updated model. In one embodiment control system 105 transmits instructions to a variable rate nutrient applicator. For example, a variable rate nutrient applicator uses the instructions to apply fertilizer and/or water at different rates in different locations within a field. In one embodiment, the instructions include mappings between location data (e.g., global positioning system (GPS) data) and fertilizer and/or water rates/values. As the applicator moves through or passes over the field, it uses current location and the mappings to dispense the fertilizer and/or water at the corresponding variable rates. In one embodiment, the variable rate nutrient applicator is an autonomous system, e.g., as described with reference to FIGS. 4-5. In some embodiments, the action includes control system 105 transmitting nutrient guidance to a user (e.g., farmer). For example, control system 105 can transmit mappings between location data (e.g., global positioning system (GPS) data) and fertilizer and/or water rates/values for a farmer to manually program or perform nutrient application and/or order nutrient supplies. In yet another embodiment, the action includes control system 105 generating an order for nutrients using the updated model. For example, control system 105 can use an amount of nutrients on hand and project an amount of nutrients needed to apply the nutrients to the field according to the updated model to determine an amount of additional nutrients needed and generate the corresponding order.

Figure 4:
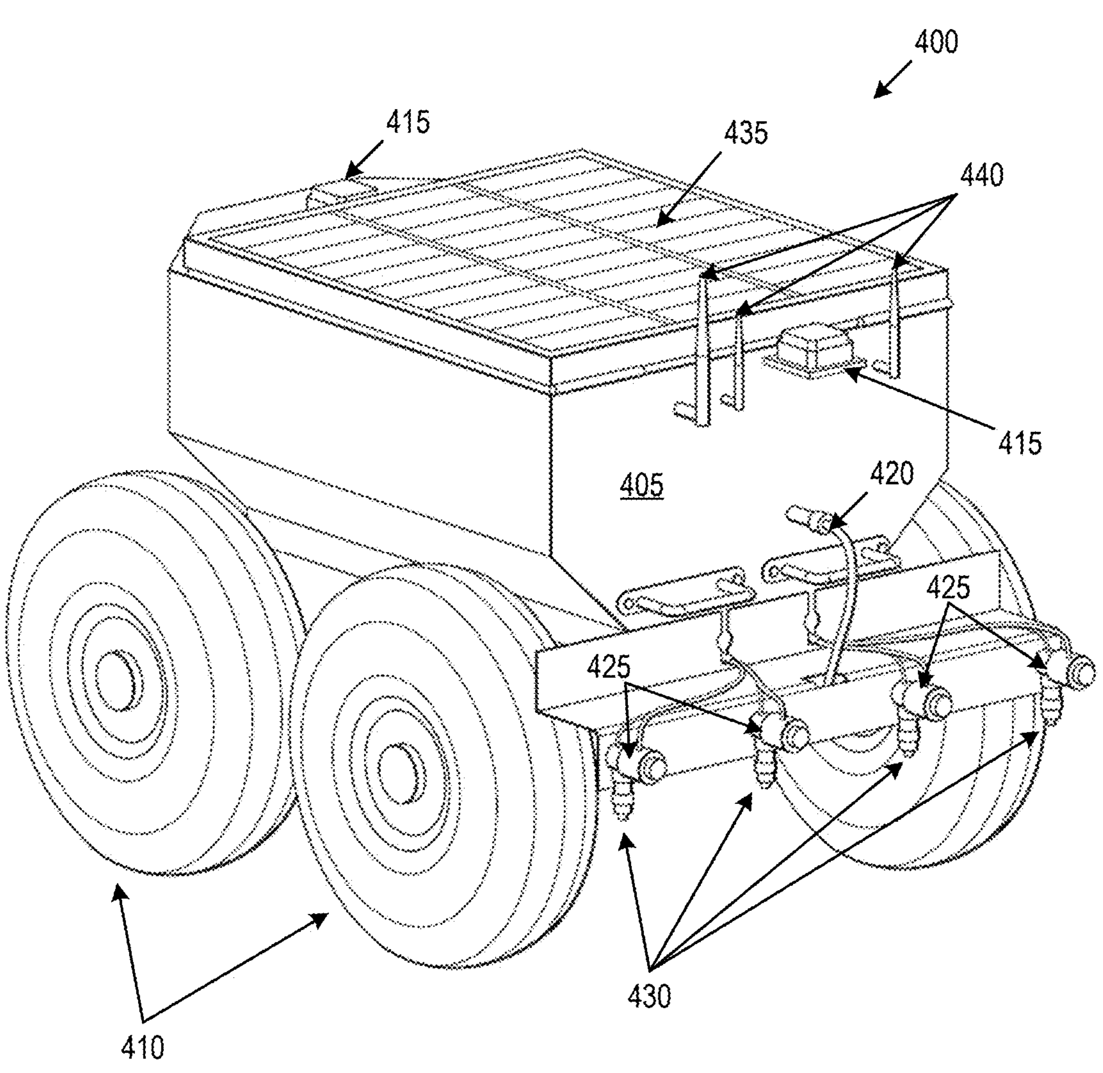
FIG. 4 illustrates an autonomous herbicide/fertilization application system in accordance with some embodiments of the present disclosure.

FIG. 4 illustrates autonomous herbicide/fertilization application system 400 in accordance with some embodiments of the present disclosure. Herbicide/fertilization application system 400 can apply herbicide, fertilizer, water, or another liquid. For ease of explanation, references below will simply refer to application system 400. While illustrated and described as a separate system from autonomous soil sampling system 100, application system 400 can include one or more of the components and capabilities of autonomous soil sampling system 100 and autonomous soil sampling system 100 can include one or more of the components and capabilities of application system 400. In some embodiments, a single autonomous platform merges the components and capabilities of both autonomous soil sampling system 100 and application system 400.

Application system 400 includes body enclosure 405. Body enclosure 405 serves as housing for (not illustrated): one or more fluid reservoirs to hold water, liquid fertilizer(s), and/or herbicide(s), one or more pumps, a power supply/battery, and a control system (e.g., similar to control system 105).

Application system 400 is a mobile platform that includes wheels 410. Similar to autonomous soil sampling system 100, the control system of application system 400 can generate output to motors attached to wheels 410 to move application system 400 in concert with navigation sensors 415. Navigation sensors 415 can include one or more of cameras, infrared sensors, radar, light detection and ranging (LIDAR), GPS, etc. to enable control system 105 to detect obstacles and autonomously navigate a field via control of wheels 410, positioning data, mapping data, etc.

Application system 400 dispenses fluid from an internal reservoir by activating/running the pump, which impels the fluid through hose 420. Hose 420 couples to one or more solenoids 425, which control the flow of the fluid through one or more nozzles 430. For example, application system 400 can use pulse width modulation (PWM) to implement short spray durations to minimize flow. Application system 400 minimizes flow by quickly providing power to (turning on) and removing power from (turning off) solenoid(s) 425. In one embodiment, application system 400 operates solenoids 425 at a frequency of 10 Hz with a 5% duty cycle (i.e., turning on one or more solenoids 425 for 5 milliseconds and turning them off for 95 milliseconds). Additionally, application system 400 can determine the PWM control of one or more solenoids 425 based on the voltage delivered to the pump (which also can be controlled via PWM for power savings), the pressure for the type of fluid to be dispensed (i.e., atmospheric pressure vs. pressurized fluid), the size of the openings in the nozzle(s) 430, etc. This enables application system 400 to dynamically maintain a low flow rate regardless of the fluid to be dispensed. As a result of this low flow rate control, application system 400 can use minimal power in dispensing fluid and dispense fluid more accurately at slow movement speeds (e.g., compared to faster flow of dispensing fluid via an applicator attached to a tractor, truck, or other large agricultural equipment).

While operating application system 400 with small nozzles 430 and a low flow rate allows for power savings and accuracy in application, it can also increase the likelihood of one or more nozzles 430 clogging. The control system of application system 400 can detect clogs and take remedial action in response to detected clogs. Clog detection and remediation of clogs are described in greater detail below with reference to FIG. 6.

In some embodiments, application system 400 includes solar panel 435 to generate additional power and extend the range and ability of application system 400 to dispense liquid. Additionally, application system 400 includes one or more wireless communication devices 440. One or more wireless communication devices 440 enable application system 400 to receive positioning data, communicate alerts to a user, receive mapping data, receive crop data, receive liquid data, receive application area boundaries, etc. For example, as described further below, application system 400 can generate a user alert or share mapping data in response to detecting a clogged nozzle 430.

Figure 5:
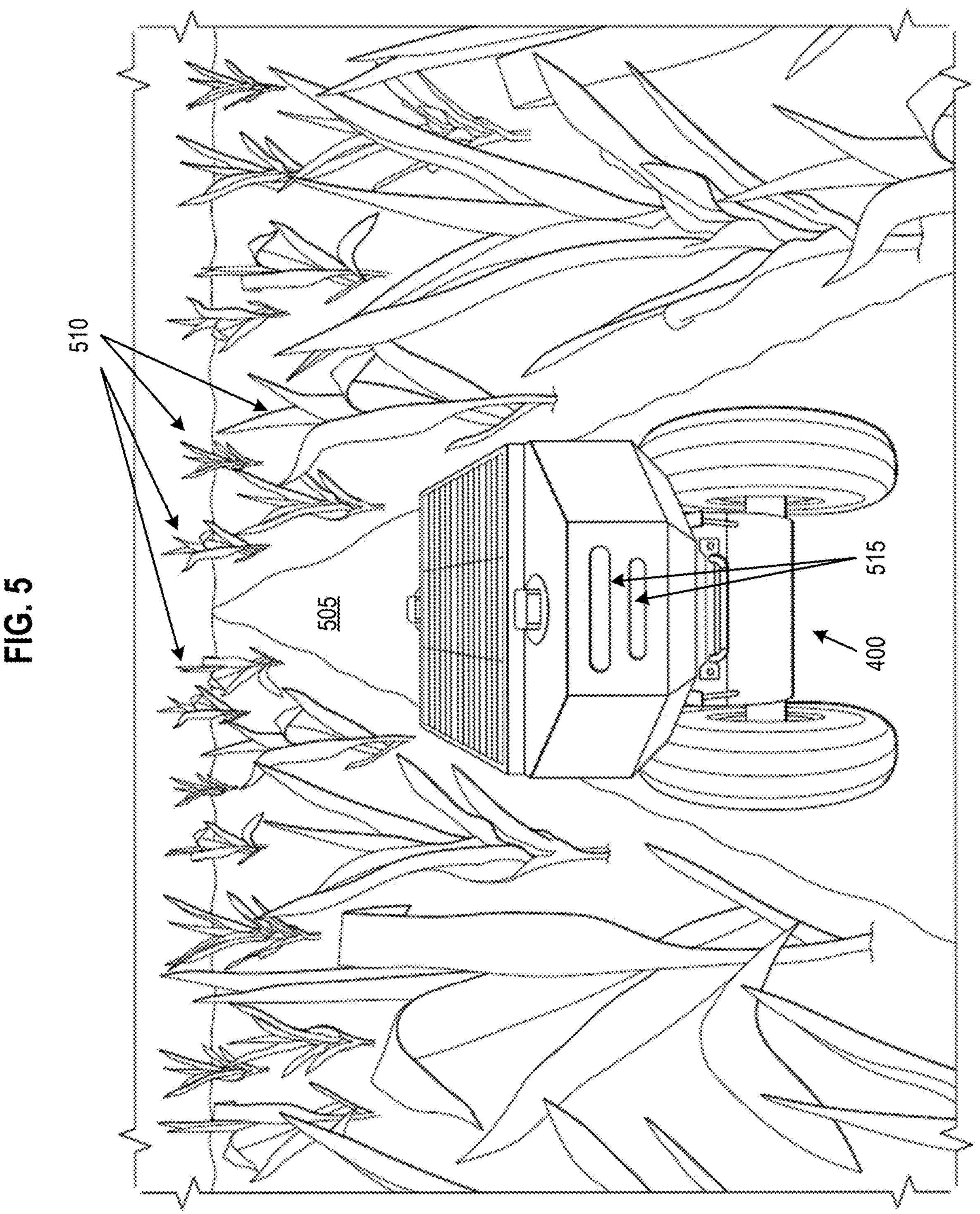
FIG. 5 another view of the autonomous herbicide/fertilization application system in accordance with some embodiments of the present disclosure.

FIG. 5 another view of autonomous application system 400 in accordance with some embodiments of the present disclosure. In this view, additional navigation sensors/cameras and lighting 515 are illustrated. As described above, application system 400 is sized to freely navigate crop rows 505 without harming crop plants 510. In some embodiment, application system 400 is less than 30 inches in width to facilitate such navigation of crop plants 510.

Figure 6:
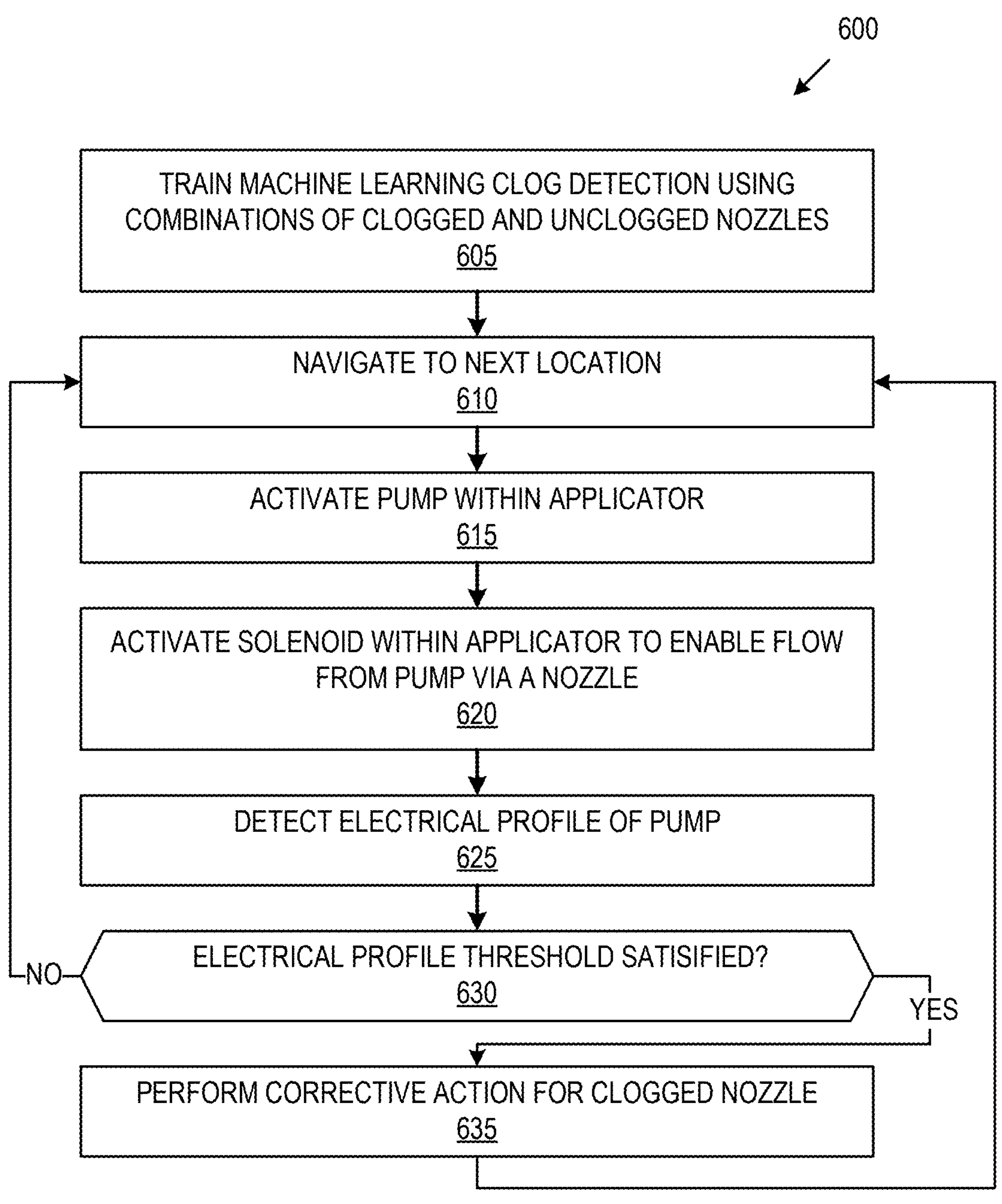
FIG. 6 is a flow diagram of an example method of detecting and correcting a clogged applicator in the autonomous herbicide/fertilization application system in accordance with some embodiments of the present disclosure.

FIG. 6 is a flow diagram of example method 600 of detecting and correcting a clogged applicator in the autonomous herbicide/fertilization application system in accordance with some embodiments of the present disclosure. Method 600 can be performed by processing logic that can include hardware (e.g., processing device, circuitry, dedicated logic, programmable logic, microcode, hardware of a device, integrated circuit, etc.), software (e.g., instructions run or executed on a processing device), or a combination thereof. In some embodiments, method 600 is performed by a control system of application system 400. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At operation 605, application system 400 receives input to train a clog detection algorithm. For example, the control system of application system 400 can include a machine learning algorithm to detect the electrical profile of an onboard pump in combinations of different conditions and training data mapping a given combination to data on the state of one or more nozzles 430. When application system 400 opens a solenoid 425 and the pump impels fluid through hose 420 and the nozzle 430, the control system detects an amount of change in the amperage or voltage drawn by the pump when the solenoid opens. For example, an unclogged nozzle 430 should allow fluid to flow, which corresponds to a transient increase in amperage/voltage drawn by the pump. In one embodiment, the training includes running the pump with simulated states of different combinations of clogged and unclogged nozzles 430 and providing training data to map the detected pump electrical profiles to the corresponding simulated states. For example, partial and/or complete clogs can be simulated by blocking the path from hose 420 to one or more nozzles 430, installing one or more nozzles 430 with smaller apertures than used in the field, etc.

In some embodiments, training is complete when the application system 400 generates a predicted output using the training input within an acceptable range of error. That is, the application system 400 tracks the pump electrical profile for each training input and generates a predicted output of which, if any, of the one or more nozzles 430 are clogged. Each training iteration or batch of training iterations, application system 400 receives/generates feedback on errors between the predicted output (clogs detected by the algorithm) and training output (e.g., the known state of clogged/unclogged nozzles 430). The feedback is used to update the clog detection algorithm using, e.g., backpropagation. Additionally, application system 400 can receive training input and output data for electrical profile indicative of a pump failure. Over a number of training iterations during the training period, application system 400 develops statistical correlations that cause a predicted output to converge with the training output, by virtue of iteratively reducing the error between the predicted output and the training output.

In some embodiments, application system 400 has a return path to the tank and a pressure regulator to enable pressure regulation at the nozzles and to perform continuous agitation of the chemical contents of the tank. In these embodiments, nozzle activation may have less impact on transient pump voltage and current. As a result, the application system 400 can activate this additional solenoid to close off the return path and ensure nozzle activations affect pump power in predictable ways for clog detection.

In some embodiments, application system 400 uses additional data to generate a predicted output. For example, application system 400 can use a known size of the opening in one or more nozzles 430, a temperature when activating the solenoid(s) 425 (i.e., temperature can impact flow), the type of liquid in the reservoir, etc. In other embodiments, application system 400 receives training in the form of a look-up table or other data structure mapping electrical profile values/ranges to corresponding states of zero, one, two, etc. clogged nozzles 430.

At operation 610, application system 400 navigates to the next application location. For example, trained application system 400 is deployed in a field and autonomously navigates the field. Similar to the description of autonomous soil sampling system 100 above, application system 400 can use mapping data, its current location (e.g., determined via an onboard positional sensor), determine a path to search for plants to which to apply the onboard fertilizer/herbicide, and generate motor outputs to control wheels 115 in conjunction with navigation sensors to drive application system 400 along that path until a plant is detected. Like the clog detection algorithm, the control system of application system 400 can include a plant detection machine learning algorithm that classifies objects in data received via an onboard camera or similar sensor 415. Application system 400 undergoes supervised learning to identify individual plants and classify the plants as, e.g., types of crop plants or types of weeds. In particular, application system 400 classifies individual pixels in the data as belonging to a plant instance and uses training iterations and feedback to develop statistical correlations that cause predicted outputs of plant detection to converge with training outputs.

In some embodiments, application system 400 navigates to a location received as input. For example, application system 400 can receive a soil sample location from autonomous soil sampling system 100 and navigate to that location to apply water and/or fertilizer to the soil sampling location. Application system 400 can send confirmation of the application, including a time stamp and quantity of liquid applied to the soil sample location, back to autonomous soil sampling system 100 for use in calibration, as discussed above.

At operation 615, application system 400 activates the onboard pump. In some embodiments, application system 400 runs the onboard pump continuously (e.g., starting upon being powered on). In some embodiments, application system 400 activates the onboard pump when approaching a target location for dispensing a liquid. For example, application system 400 navigates from a starting location to a field targeted for herbicide and/or fertilizer application and applies power to the pump in anticipation of applying the liquid(s).

At operation 620, application system 400 activates one or more solenoids 425 to dispense the liquid. For example, upon detecting a weed, application system 400 positions itself such that one or more nozzles 430 can apply herbicide to the detected weed. As discussed above, application system 400 minimizes power consumption by using PWM to apply the herbicide (or other liquid) at a low flow rate that corresponds to application system 400 being stationary or moving at a slow speed.

At operation 625, application system 400 detects any change in the electrical profile of the pump in response to the activation of the one or more solenoids 425. For example, application system 400 detects a change in voltage or amperage drawn by the pump when the solenoid(s) 425 open.

At operation 630, application system 400 determines if an electrical profile threshold has been satisfied. For example, application system 400 uses the detected electrical profile and corresponding activation of one or more nozzles 430 as inputs to the trained clog detection algorithm. If the change in the electrical profile correlates with an electrical profile of no clogged nozzles 430, application system 400 determines that the electrical profile threshold for a clog has not been satisfied and the flow returns to operation 610. In other words, application system 400 is operating normally and can continue to the next location for a liquid application. If the change in the electrical profile correlates with an electrical profile for a clog in one or more nozzles 430, application system 400 determines that the electrical profile threshold for a clog has been satisfied and the flow proceeds to operation 635. Similarly, application system 400 can determine if an electrical profile threshold for pump failure has been satisfied.

At operation 635, application system 400 performs a corrective action for one or more clogged nozzles 430 and/or pump failure. For example, corrective actions can include testing individual nozzles 430 one at a time to isolate which are clogged (e.g., if the clog detection occurred while using multiple nozzles 430, application system 400 can repeat operations 620-630 for one or more nozzles 430 individually), applying the liquid to the location using another nozzle 430 that has not been detected as being clogged, altering the PWM or other control of other nozzle(s) 430 to compensate for a perceived lack of flow due to detected clog(s). Alternatively, or in addition to these autonomous actions, application system 400 can generate an alert to a user of a detected clog, navigate to a location for user correction of a clogged nozzle or pump failure, and/or save and/or transmit a location where the clog/failure occurred to enable later application of the liquid (manually or automatically) at a later time.

FIG. 7 is a flow diagram of example method 700 of herbicide application in accordance with some embodiments of the present disclosure. Method 700 can be performed by processing logic that can include hardware (e.g., processing device, circuitry, dedicated logic, programmable logic, microcode, hardware of a device, integrated circuit, etc.), software (e.g., instructions run or executed on a processing device), or a combination thereof. In some embodiments, method 700 is performed by a control system of application system 400. Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At operation 705, application system 400 receives training data mapping weed characteristics to herbicide application strategies. For example, application system 400 receives a data structure or model that maps weed characteristics to herbicide application strategies. Weed characteristics include, e.g., weed type, weed height/size, density of weeds, morphological features such as presence of leaves on weed vs. grass, weed maturity, weed proximity to one or more desirable plants, soil characteristics such as pH and/or recent fertilization, timing and amount of water in the form of recent irrigation, precipitation, and/or humidity, weather data such as recent/current/projected temperature and/or sun exposure, the time of day and/or year, etc. Herbicide strategies include, e.g., herbicide type, herbicide concentration/ratio to water, applicator nozzle type, flow rate/application amount, system movement speed during application, spray angle, single vs. multiple application, etc. In one embodiment, the training data maps individual characteristics and/or combinations of characteristics to individual and/or combinations of herbicide strategies.

In one embodiment, the training data is the result of training a machine learning algorithm to identify weed characteristics using, e.g., camera images of plants. For example, algorithm processes the images to enhance quality, resize, normalize, and/or extract features. The algorithm receives user input identifying characteristics in the images and creates correlations between the extracted features and received characteristics using a classification algorithm, neural network, or the like. The training can further include iterations of the algorithm receiving feedback on correlations to fine tune the algorithm's ability to accurately identify weed types, weed features, desirable plants, detect features of dying weeds (described further below), etc.

Similarly, the training data can be the result of training a machine learning algorithm to correlate weed characteristics (both visual characteristics discussed above and other input data, such as the state of soil, time of day, time of year, temperature, geographical location, etc.) to herbicide application strategies. In one example, a strategy for determining application rate for a kochia weed in western Kansas in July is initially modeled in training data as a linear function of an amount of herbicide to apply to the weed based on the height of the weed. In another example, the correlation of characteristic(s) to herbicide strategy includes a confidence value. When the confidence value for a strategy for a given herbicide is below a threshold value, the training can use initial confidence values to set up application system 400 to determine the optimal herbicide/concentration for eliminating a given weed. For example, the training data for henbit weeds in northwestern Texas can start with multiple herbicides/concentrations and the optimal herbicide/concentration is determined using a separate model for each herbicide/concentration. As discussed below, application system 400 computes the probability of the optimal spray strategy for each herbicide achieving elimination through experimentation with different instances of the weed type and evaluating results.

At operation 710, application system 400 navigates to the next location within a field. For example, application system 400 uses mapping data, its current location (e.g., determined via an onboard positional sensor), to determine a path through a field and generates motor outputs to control wheels 410 in conjunction with navigation sensors 415/515 to locate the next weed. Application system uses the training data for weed identification and a navigation sensor, such as a camera, and lighting 515 to detect a weed as discussed further below.

At operation 715, application system 400 detects a first weed using an onboard camera or similar navigation sensor. For example, as navigating the field, application system 400 processes images of surrounding plants captured by camera 515. In one embodiment, application system 400 uses onboard lighting to improve the images captured by the camera. As discussed above, application system 400 can process images to quality, resize, normalize, and/or extract features. Using the training data, application system 400 maps extracted features to plant characteristics and identifies desirable plants/types and weeds/types. In one embodiment, application system 400 identifies the first weed via processing the feed of images captured by camera 515 and navigates within a threshold proximity of the weed to apply herbicide if/as determined below.

At operation 720, application system 400 identifies one or more characteristics of the weed and/or environment. For example, application system 400 uses the image of the weed captured above or, after navigating within the threshold proximity of the weed, obtains one or more additional images of the weed. Using the training data, application system 400 identifies one or more characteristics of the first weed. As discussed above, the identified characteristics can include weed features (leaves, height, etc.), distances between desirable plants and weeds, etc. Additionally, application system 400 can use location data, time/date data, meteorological data, one or more onboard sensors (e.g., thermometer, electrometric sensor, etc.), measurements taken by another system (e.g., autonomous soil sampling system 100), and other inputs to identify the characteristic(s).

At operation 725, application system 400 determines an herbicide application strategy using the characteristic(s). For example, application system 400 uses the training data to map the characteristic(s) identified for the first weed to one or more herbicide application strategies. If the characteristic(s) map to multiple herbicide application strategies, application system 400 selects one of the strategies for experimentation. For example, application system 400 selects one of the strategies using data saved indicating one or more recent strategies used based on the characteristic(s), based on confidence values associated with the strategies, by way of random selection, round robin, and/or another selection algorithm.

At operation 730, application system 400 applies herbicide to the weed in accordance with the strategy. For example, application system 400 selects the herbicide onboard (if it carries multiple herbicides) by activating a solenoid to allow an onboard pump to move the herbicide to one or more nozzles 430. Additionally, the herbicide strategy can control the concentration of herbicide applied. For example, application system 400 can use the herbicide application strategy to determine an amount of water (when stored onboard separately from the concentrated herbicide) to mix with the herbicide while applying the herbicide to the weed.

Based on the strategy and location of the weed relative to application system 400, application system 400 selects which of the nozzles 430 to use to dispense the herbicide and activates the corresponding solenoid(s). In one embodiment, application system 400 adjusts a spray angle of one or more nozzles 430 in accordance with the strategy. For example, a contact herbicide may be applied directly to leaves of the weed while a systemic herbicide may be applied to the weed as well as the soil around the weed to facilitate root absorption. In some embodiments, application system 400 uses different nozzles 430 to apply the herbicide at different angles. In other embodiments, application system 400 mechanically adjusts the spray angle of a nozzle 430 using a motor, servo, or similar mechanism. Additionally, application system 400 can use the proximity of the weed to desirable plant(s) to adjust/select the spray angle.

As another example, the herbicide application strategy can further control the amount of herbicide applied to the weed. Application system 400 controls the amount of herbicide applied by controlling the flow rate of each nozzle (e.g., via pulse width modulation control of nozzle solenoids), the number of nozzles used to apply the herbicide, the type of nozzle used, the amount of time the herbicide flows via each nozzle, and/or a movement speed of application system 400 relative to the weed while applying herbicide.

In yet another example, the herbicide application strategy controls a number of application steps. For example, the herbicide application strategy can cause application system 400 to apply herbicide in multiple passes, steps, or otherwise divide the application in multiple applications.

In some embodiments, the herbicide application strategy includes bypassing a current application of herbicide to a weed. For example, the strategy can include a minimum height, size, inclusion of leaves, or other maturity threshold for a weed. If the weed does not satisfy the maturity threshold, application system 400 skips the application of herbicide on that weed until the weed satisfies the maturity threshold.

At operation 735, application system 400 continues to navigate the field and apply herbicide to other weeds. For example, application system 400 saves a record of the application of herbicide to the first weed, such as the weed location, the strategy used, a timestamp of the application of the strategy, etc. and navigates to the next weed to continue applying herbicide to weeds in the field according to operations 710-730 described above.

At operation 740, application system 400 navigates back to the location of the first weed. For example, application system 400 navigates back to the location of the first weed using the saved location data associated with the application of herbicide to the first weed. In one embodiment, application system 400 navigates back to the location of the first weed in response to completing a navigation of the field or a portion thereof. In other embodiments, application system 400 navigates back to the location of the first weed in response to a threshold amount of time passing following the application of the herbicide application strategy to the first weed. For example, application system 400 can compare an amount of time that has elapsed following the application of the herbicide application strategy to the first weed and compare that amount of time to a threshold amount of time saved. In one embodiment, the threshold amount of time represents an estimated amount of time for the herbicide to effectively kill the weed. In another embodiment, the threshold amount of time is an amount of time between applications of herbicide for effective treatment of the weed according to the herbicide application strategy.

At operation 745, application system 400 detects the condition of the first weed after the prior application of the herbicide strategy. For example, application system 400 determines if the prior application of herbicide killed the first weed. In one embodiment, application system 400 determines if the herbicide killed or is killing the first weed by using the training data and the onboard camera to determine if the first weed is still present and, if so, symptoms represented by color, size, and or structure of the first weed. For example, twisting of the leaf stalks, leaves turning yellow or brown, leaf curling/distortion, etc. can be symptoms of the impact of the prior application of herbicide. In some embodiments, application system 400 determines the herbicide killed the first weed when the first weed is no longer present or is present with symptoms that satisfy a threshold of, e.g., discoloration and/or structural change. In some embodiments, application system 400 determines a partial success of the herbicide application when some symptoms of the weed dying are present (e.g., discolored and/or deformed leaves) while another portion of the weed appears unaffected.

In some embodiments, application system 400 detects the condition of the first weed to determine if the weed has reached a threshold level of maturity for application of the herbicide. For example, as discussed above, application system 400 can skip the application of herbicide according to the herbicide application strategy when the first weed does not satisfy the maturity threshold. Accordingly, application system 400 can save the location of the first weed and iteratively return to the weed until the weed satisfies the maturity threshold and then treat the weed with herbicide.

At operation 750, application system 400 updates the herbicide application strategy for the characteristic(s) when the condition of the first weed meets an update threshold. For example, application system 400 updates one or more of: herbicide type, herbicide concentration/ratio to water, applicator nozzle type, flow rate/application amount, system movement speed during application, spray angle, single vs. multiple application, etc. in response to determining whether the weed is dying or died as a result of the herbicide application, only a portion of the weed is dying, or another indication of success, partial success, or failure of the herbicide application strategy. The update can be to apply more herbicide, spray a greater area of/around the weed, etc. in response to determining a partially successful or unsuccessful strategy. Additionally, the update can be to apply less herbicide, spray a lesser area of/around the weed, etc. in response to determining a completely successful strategy. As a result, application system 400 can fine tune the herbicide application strategy to use the most efficient amount of herbicide, thereby minimizing cost and any negative impacts of herbicide application.

In some embodiments, application system 400 updates the herbicide application by updating one more characteristics of the strategy. For example, application system 400 can increase the amount or concentration of herbicide applied in response to the detected condition of the first weed. Continuing with the example above of the kochia weed in western Kansas, application system 400 may track one hundred applications to similar weed characteristics and determine that 40% resulted in successful elimination of the weed and 60% were unsuccessful. In response, application system 400 can update the linear function model representing the amount of herbicide to apply to the weed based on the height of the weed using the height of the weeds successfully eliminated and the height of the weeds that were not successfully eliminated. The updated linear function will, e.g., increase the amount of herbicide applied and enable application system 400 to evaluate if the updated strategy results in an increase in the percentage of weeds successfully eliminated.

In one embodiment, application system 400 updates a confidence value for the herbicide application strategy based on the condition of the first weed. For example, application system 400 increases a confidence value in the herbicide application strategy when application system 400 determines that the first weed is dead/dying following the application of herbicide according to the herbicide application strategy or decrease a confidence value in the herbicide application strategy when application system 400 determines that the first weed is not dead/dying following the application of herbicide according to the herbicide application strategy. If application system 400 is experimenting with multiple weeds of similar characteristics to determine which of multiple herbicide application strategies to use by default for those characteristics, like the henbit weed example given above, application system 400 can use a threshold number of weeds/herbicide applications and corresponding confidence value updates to select the strategy with the highest confidence value as the default herbicide application strategy for those weed characteristics.

At operation 755, application system 400 determines if an amount of onboard herbicide or water satisfies a refill threshold. For example, application system 400 can track the cumulative amount of herbicide and/or water applied in the field following the last refill and, when that amount satisfies a refill threshold amount, trigger a refill operation. In one embodiment, application system 400 determines if the refill threshold has been reached following each application of herbicide. In other embodiments, application system 400 determines if the refill threshold has been reached periodically based on a set amount of time or another trigger. If the refill threshold has not been satisfied, application system 400 continues treating weeds and method 700 returns to operation 710. If the refill threshold has been satisfied, application system 400 initiates a refill operation and method 700 proceeds to operation 760.

At operation 760, application system 400 navigates to a refilling location and receives additional herbicide. In one embodiment, the refilling location is a fixed location saved in application system 400 memory. In another embodiment, application system 400 determines the refilling location dynamically based on the current location of application system 400. For example, application system 400 determines a nearest road, open area, or similar location that is accessible by a tractor, truck, or larger vehicle. In one embodiment, application system 400 stores location data indicating accessible areas and determines a closest location within those accessible areas.

In some embodiments, application system 400 transmits a refill/rendezvous request message when navigating to the refilling location. For example, application system 400 can transmit a signal to a farmer or other user indicating the need for a refill. The signal can include one or more of the refilling location and/or the herbicide type(s) in need of refill. As a result, the farmer or other user can rendezvous with application system 400 and facilitate the refill.

If application system 400 is to continue treating weeds once refilled, method 700 proceeds to operation 710 and application system 400 navigates to the next location to continue dispensing herbicide.

Figure 8:
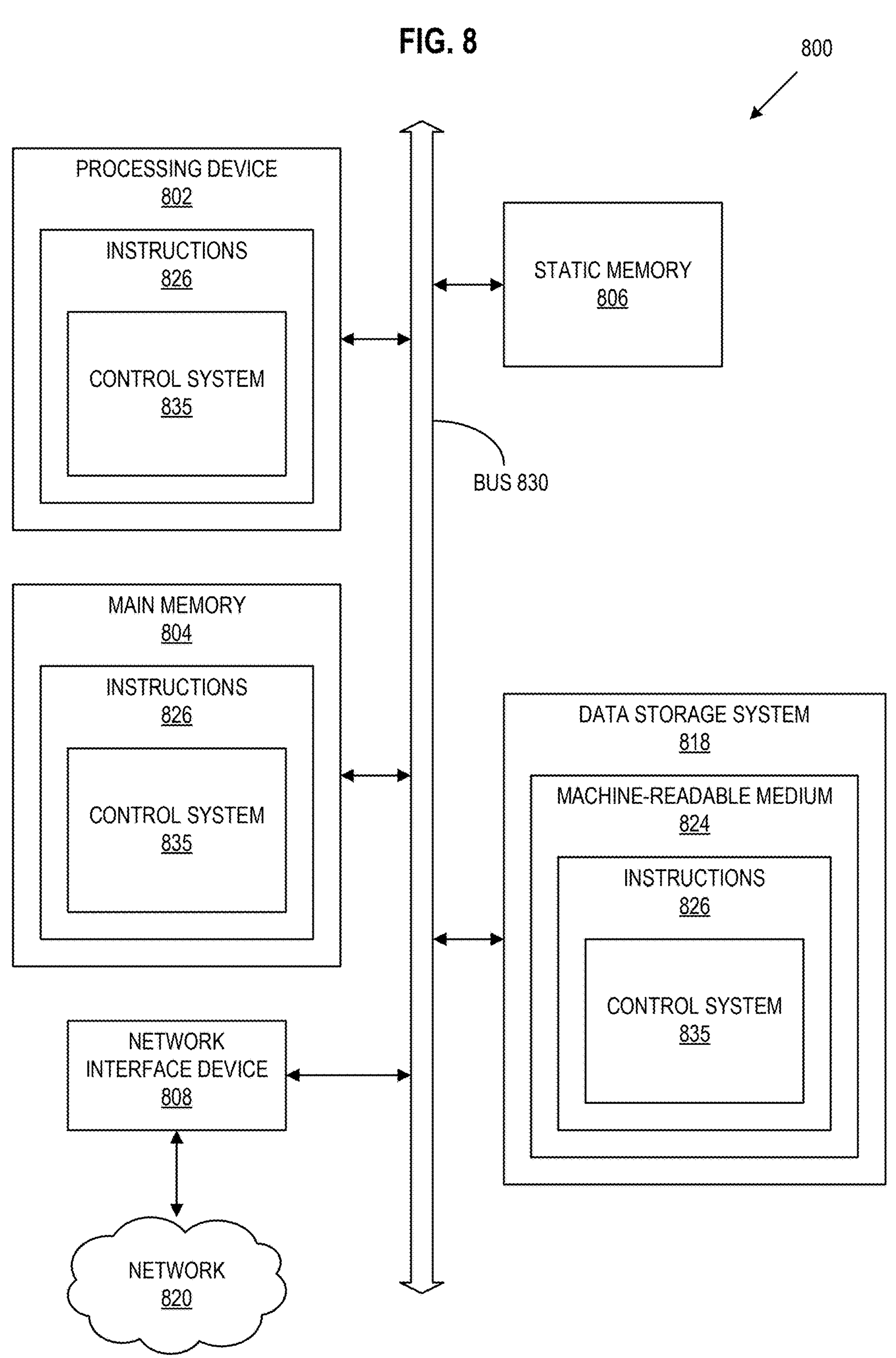
FIG. 8 is a block diagram of an example computer system in which embodiments of the present disclosure may operate.

FIG. 8 is a block diagram of example computer system 800 within which a set of instructions, for causing the machine to perform any one or more of the methodologies discussed herein, can be executed. In some embodiments, computer system 800 can correspond to a control system (e.g., control system 105 or a corresponding control system of application system 400) to perform operations described herein. In alternative embodiments, the machine can be connected (e.g., networked) to other machines in a LAN, an intranet, an extranet, and/or the Internet. The machine can operate in the capacity of a server or a client machine in client-server network environment, as a peer machine in a peer-to-peer (or distributed) network environment, or as a server or a client machine in a cloud computing infrastructure or environment.

The machine can be a computer or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

Computer system 800 includes processing device 802, main memory 804 (e.g., read-only memory (ROM), flash memory, dynamic random access memory (DRAM) such as synchronous DRAM (SDRAM) or Rambus DRAM (RDRAM), etc.), static memory 806 (e.g., flash memory, static random access memory (SRAM), etc.), and data storage system 818, which communicate with each other via bus 830.

Processing device 802 represents one or more general-purpose processing devices such as a microprocessor, a central processing unit, or the like. More particularly, the processing device can be a complex instruction set computing (CISC) microprocessor, reduced instruction set computing (RISC) microprocessor, very long instruction word (VLIW) microprocessor, or a processor implementing other instruction sets, or processors implementing a combination of instruction sets. Processing device 802 can also be one or more special-purpose processing devices such as an application specific integrated circuit (ASIC), a field programmable gate array (FPGA), a digital signal processor (DSP), network processor, or the like. Processing device 802 is configured to execute instructions 826 for performing the operations and steps discussed herein. Computer system 800 can further include network interface device 808 to communicate over network 820.

Data storage system 818 can include machine-readable storage medium 824 (also known as a non-transitory computer-readable storage medium) on which is stored one or more sets of instructions 826 or software embodying any one or more of the methodologies or functions described herein. Instructions 826 can also reside, completely or at least partially, within main memory 804 and/or within processing device 802 during execution thereof by computer system 800, main memory 804 and processing device 802 also constituting machine-readable storage media.

In one embodiment, instructions 826 include instructions to implement functionality corresponding to autonomous soil sampling system 100 and/or application system 400. For example, instructions 826 can include control system 835 corresponding to control system 105 and/or a control system of application system 400. While machine-readable storage medium 824 is shown in an example embodiment to be a single medium, the term "machine-readable storage medium" should be taken to include a single medium or multiple media that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media, and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. The present disclosure can refer to the action and processes of a computer system, or similar electronic computing device, that manipulates and transforms data represented as physical (electronic) quantities within the computer system's registers and memories into other data similarly represented as physical quantities within the computer system memories or registers or other such information storage systems.

The present disclosure also relates to an apparatus for performing the operations herein. This apparatus can be specially constructed for the intended purposes, or it can include a general-purpose computer selectively activated or reconfigured by a computer program stored in the computer. For example, a computer system or other data processing system may carry out the computer-implemented methods 300, 600, and 700 in response to its processor executing a computer program (e.g., a sequence of instructions) contained in a memory or other non-transitory machine-readable storage medium. Such a computer program can be stored in a computer readable storage medium, such as, but not limited to, any type of disk including floppy disks, optical disks, CD-ROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

The algorithms and displays presented herein are not inherently related to any particular computer or other apparatus. Various general-purpose systems can be used with programs in accordance with the teachings herein, or it can prove convenient to construct a more specialized apparatus to perform the method. The structure for a variety of these systems will appear as set forth in the description below. In addition, the present disclosure is not described with reference to any particular programming language. It will be appreciated that a variety of programming languages can be used to implement the teachings of the disclosure as described herein.

The present disclosure can be provided as a computer program product, or software, that can include a machine-readable medium having stored thereon instructions, which can be used to program a computer system (or other electronic devices) to perform a process according to the present disclosure. A machine-readable medium includes any mechanism for storing information in a form readable by a machine (e.g., a computer). In some embodiments, a machine-readable (e.g., computer-readable) medium includes a machine (e.g., a computer) readable storage medium such as a read only memory ("ROM"), random access memory ("RAM"), magnetic disk storage media, optical storage media, flash memory components, etc.

In the foregoing specification, embodiments of the disclosure have been described with reference to specific example embodiments thereof. It will be evident that various modifications can be made thereto without departing from the broader spirit and scope of embodiments of the disclosure as set forth in the following claims. The specification and drawings are, accordingly, to be regarded in an illustrative sense rather than a restrictive sense.

What is claimed is:

1. A method comprising:

detecting, by an autonomous applicator system at a first time, a weed at a first location within a field;

identifying, by the autonomous applicator system, one or more characteristics of the weed and/or environment;

determining, by the autonomous applicator system, an herbicide application strategy for the weed based on the one or more characteristics;

activating a solenoid within the applicator system to enable a flow of herbicide via an applicator nozzle to treat the weed in accordance with the herbicide application strategy;

navigating, by the autonomous applicator system, back to the first location from another location at a second time after treating the weed in accordance with the herbicide application strategy;

detecting, by the autonomous applicator system, a condition of the weed at the first location at the second time; and updating the herbicide application strategy for the one or more characteristics in response to the condition of the weed at the first location at the second time, wherein the updating causes the autonomous applicator system to change how herbicide is subsequently applied to weeds having the one or more characteristics.

2. The method of claim 1, wherein the one or more characteristics include: weed type, weed size, stem location, chemical mechanism of the herbicide, proximity of the weed to desirable plants, weed morphological features, weather data, time of year, time of day, and/or weed maturity.

3. The method of claim 1, wherein updating the herbicide application strategy includes changing: a herbicide type, a concentration of herbicide to water, applicator nozzle type, flow rate of the herbicide, duration of flow of the herbicide, movement speed of the autonomous applicator system, spray angle, a time between the first time and the second time, and/or number of applications of the herbicide.

4. The method of claim 1, wherein updating the herbicide application strategy is implemented via machine learning algorithm, the method further comprising:

receiving training data mapping weed characteristic combinations to herbicide application strategies.

5. The method of claim 1, wherein the updating the herbicide application strategy includes increasing or decreasing a confidence value associated with the herbicide application strategy, and wherein the herbicide application strategy is one of multiple herbicide application strategies mapped to the one or more characteristics.

6. The method of claim 5, further comprising:

determining the confidence value associated with the herbicide application strategy satisfies a threshold; and selecting the herbicide application strategy over others of the multiple herbicide application strategies to be a default herbicide application strategy for the one or more characteristics.

7. The method of claim 1, further comprising:

determining, by the autonomous applicator system, an amount of herbicide applied satisfies a threshold; and navigating to an herbicide refill location in response to determining the amount satisfies the threshold.

8. The method of claim 7, further comprising:

transmitting a message to a user a rendezvous request at the refill location to facilitate a refilling of the herbicide.

9. A non-transitory computer-readable storage medium comprising instructions that, when executed by a processing device, cause the processing device to:

detect a weed at a first location of an autonomous applicator system within a field at a first time;

identify one or more characteristics of the weed and/or environment;

determine an herbicide application strategy for the weed based on the one or more characteristics;

activate a solenoid within the applicator system to enable a flow of herbicide via an applicator nozzle to treat the weed in accordance with the herbicide application strategy;

navigate the autonomous applicator system back to the first location from another location at a second time after treating the weed in accordance with the herbicide application strategy;

detect a condition of the weed at the first location at the second time; and update the herbicide application strategy for the one or more characteristics in response to the condition of the weed at the first location at the second time, wherein the updating causes the autonomous applicator system to change how herbicide is subsequently applied to weeds having the one or more characteristics.

10. The non-transitory computer-readable storage medium of claim 9, wherein the one or more characteristics include: weed type, weed size, stem location, chemical mechanism of the herbicide, proximity of the weed to desirable plants, weed morphological features, weather data, time of year, time of day, and/or weed maturity.

11. The non-transitory computer-readable storage medium of claim 9, wherein updating the herbicide application strategy includes changing: a herbicide type, a concentration of herbicide to water, applicator nozzle type, flow rate of the herbicide, duration of flow of the herbicide, movement speed of the autonomous applicator system, spray angle, a time between the first time and the second time, and/or number of applications of the herbicide.

12. The non-transitory computer-readable storage medium of claim 9, wherein updating the herbicide application strategy is implemented via machine learning algorithm, wherein the processing device is further to:

receive training data mapping weed characteristic combinations to herbicide application strategies.

13. The non-transitory computer-readable storage medium of claim 9, wherein the updating the herbicide application strategy includes increasing or decreasing a confidence value associated with the herbicide application strategy, and wherein the herbicide application strategy is one of multiple herbicide application strategies mapped to the one or more characteristics.

14. The non-transitory computer-readable storage medium of claim 13, wherein the processing device is further to:

determine the confidence value associated with the herbicide application strategy satisfies a threshold; and select the herbicide application strategy over others of the multiple herbicide application strategies to be a default herbicide application strategy for the one or more characteristics.

15. The non-transitory computer-readable storage medium of claim 13, wherein the processing device is further to:

determine an amount of herbicide applied by the autonomous applicator system satisfies a threshold;

navigate the autonomous applicator system to an herbicide refill location in response to determining the amount satisfies the threshold; and transmit a message to a user a rendezvous request at the refill location to facilitate a refilling of the herbicide.

16. An autonomous herbicide applicator system comprising:

an applicator nozzle;

a solenoid within the applicator system to enable a flow of herbicide via the applicator nozzle;

a memory device; and a processing device, operatively coupled with the memory device, to:

detect a weed at a first location of an autonomous applicator system within a field at a first time;

identify one or more characteristics of the weed and/or environment;

determine an herbicide application strategy for the weed based on the one or more characteristics;

activate the solenoid within the applicator system to enable a flow of herbicide via the applicator nozzle to treat the weed in accordance with the herbicide application strategy;

navigate the autonomous applicator system back to the first location from another location at a second time after treating the weed in accordance with the herbicide application strategy;

detect a condition of the weed at the first location at the second time; and update the herbicide application strategy for the one or more characteristics in response to the condition of the weed at the first location at the second time, wherein the updating causes the autonomous applicator system to change how herbicide is subsequently applied to weeds having the one or more characteristics.

17. The autonomous herbicide applicator system of claim 16, wherein the one or more characteristics include: weed type, weed size, stem location, chemical mechanism of the herbicide, proximity of the weed to desirable plants, weed morphological features, weather data, time of year, time of day, and/or weed maturity.

18. The autonomous herbicide applicator system of claim 16, wherein updating the herbicide application strategy includes changing: a herbicide type, a concentration of herbicide to water, applicator nozzle type, flow rate of the herbicide, duration of flow of the herbicide, movement speed of the autonomous applicator system, spray angle, a time between the first time and the second time, and/or number of applications of the herbicide.

19. The autonomous herbicide applicator system of claim 16, wherein updating the herbicide application strategy is implemented via machine learning algorithm, wherein the processing device is further to:

receive training data mapping weed characteristic combinations to herbicide application strategies.

20. The autonomous herbicide applicator system of claim 16, wherein the updating the herbicide application strategy includes increasing or decreasing a confidence value associated with the herbicide application strategy, wherein the herbicide application strategy is one of multiple herbicide application strategies mapped to the one or more characteristics, and wherein the processing device is further to:

determine the confidence value associated with the herbicide application strategy satisfies a threshold; and select the herbicide application strategy over others of the multiple herbicide application strategies to be a default herbicide application strategy for the one or more characteristics.

* * * * *